Figure 1:
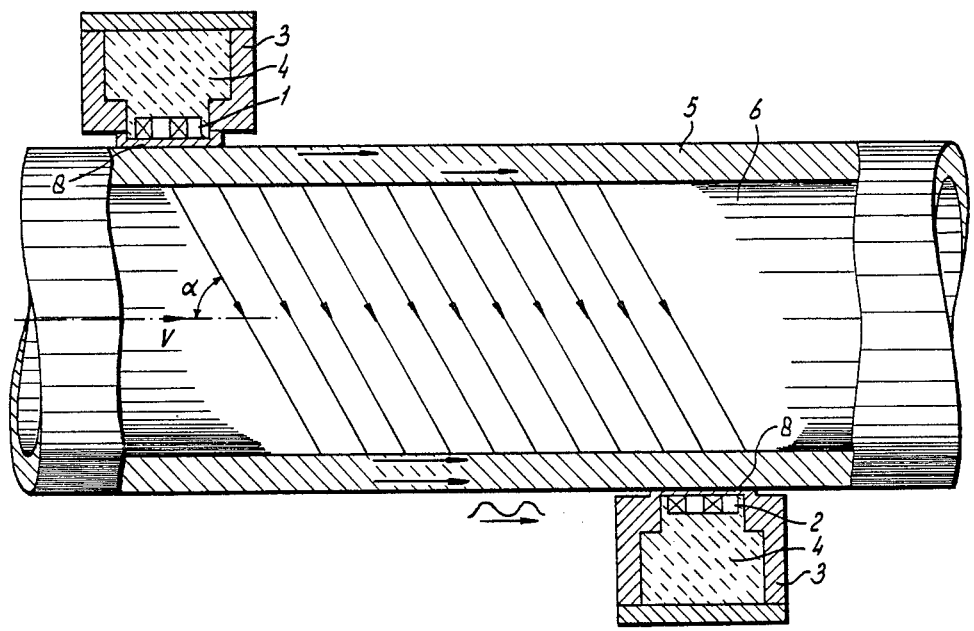

United States Patent [19]
Herremans et al.

[11] Patent Number: 4,838,127
[45] Date of Patent: Jun. 13, 1989

[54] ULTRASONIC FLOW METER

[75] Inventors: Pieter Herremans, Alblasserdam; Christiaan J. Hoogendijk, Sleeuwijk; Adriaan H. Boer, Sliedrecht; Aart J. Van Bekkum, Hoornaar, all of Netherlands

[73] Assignee: Altometer, Produktiebedrijf Van Rheometron A.G., Netherlands

[21] Appl. No.: 101,263

[22] Filed: Sep. 25, 1987

[30] Foreign Application Priority Data

Sep. 29, 1986 [NL] Netherlands .......................... 8602458

[51] Int. Cl.$^4$ ............................................. G01F 1/66
[52] U.S. Cl. .................................... 73/861.28; 73/642
[58] Field of Search ................ 73/861.28, 861.27, 642, 73/644; 310/334, 335

[56] References Cited

U.S. PATENT DOCUMENTS

| | | | |
|---|---|---|---|
| 4,296,348 | 10/1981 | Toda | 310/334 |
| 4,375,767 | 3/1983 | Magori | 73/861.18 |
| 4,454,767 | 6/1984 | Shinkai et al. | 73/861.28 X |
| 4,467,659 | 8/1984 | Baumoel | 73/861.27 |

*Primary Examiner*—Jerry W. Myracle
*Attorney, Agent, or Firm*—Stevens, Davis, Miller & Mosher

[57] ABSTRACT

Ultrasonic flow meter of the clamp-on type for the measurement of the flow rate of a liquid in a pipeline, provided with two piezoelectric transmitting-receiving transducers, each accommodated in a housing, which are clamped at both sides of the pipeline axially offset with respect to each other thereon and which alternately transmit ultrasonic pulses into the pipeline and receive them therefrom in order to determine the flow rate from the transit time of the source pulses in the upstream and downstream direction. The transducers each consist of a row of adjacent subtransducers, the pulse emission face of which row is coupled over its entire length in the axial direction to the pipe wall. The substransducers are activated by control signals, the phase difference between the control signals at every two adjacent subtransducers and the distance between the centers thereof being matched to each other such that the transducer deforms approximately sinusoidally with a periodic length which corresponds to the wavelength $\lambda$ of Lamb surface waves to be generated in the pipe wall in the $A_0$ mode. The waves propagate in the axial direction along the pipe wall and, on the inside thereof, are converted into longitudinal waves in the adjacent liquid.

4 Claims, 3 Drawing Sheets

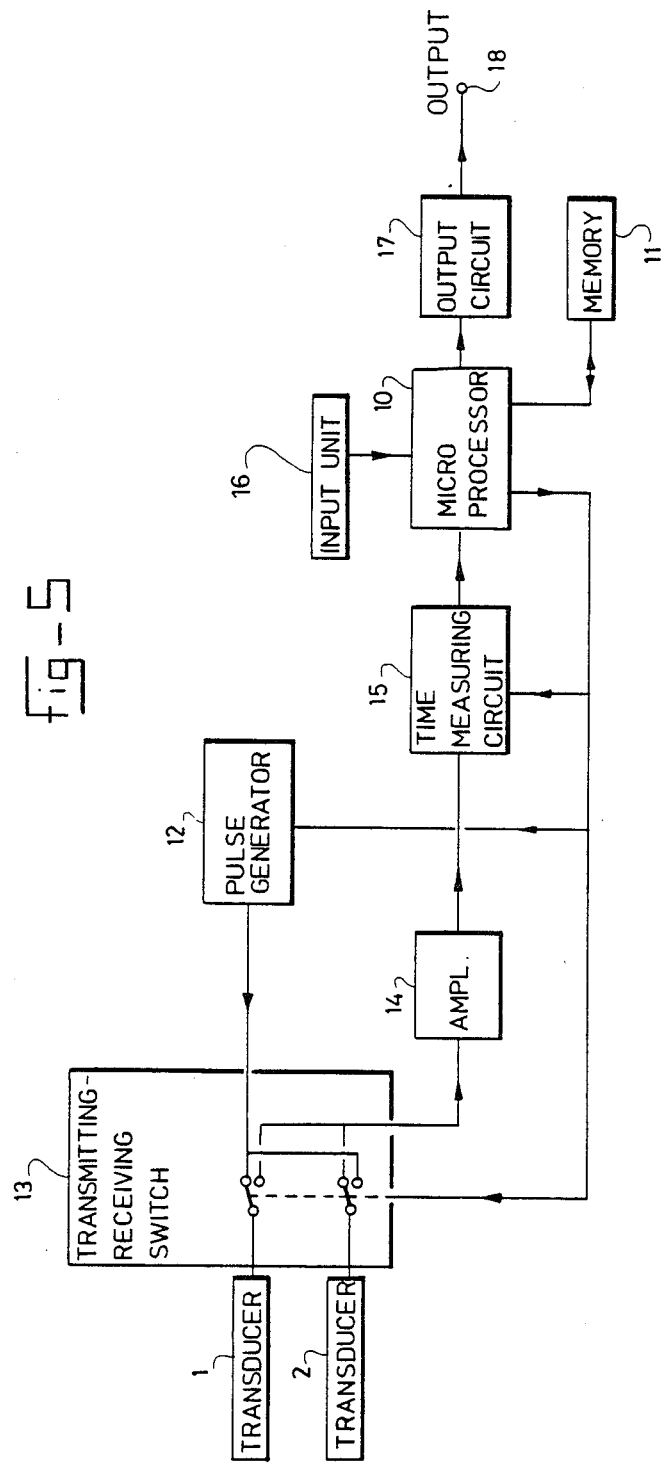

ULTRASONIC FLOW METER

The invention relates to an ultrasonic flow meter of the clamp-on type for the measurement of the flow rate of a liquid in a pipeline, provided with two piezoelectric transmitting-receiving transducers, each accommodated in a housing intended for the purpose, which are clamped at both sides of the pipeline axially offset with respect to each other thereon and which alternately transmit ultrasonic pulses into the pipeline and receive them therefrom in order to determine the flow rate from the transit time of the sonic pulses in the upstream and downstream direction. Such an ultrasonic flow meter is known from U.S. Pat. No. 4,467,659.

The piezoelectric transducers used in the ultrasonic flow meter known from the above-mentioned patent are each at an angle with respect to the pipe wall and arranged at some distance therefrom in the housing. In this case, sonic waves of the shear mode type are transmitted into the surface of the pipe wall. The emission faces of the piezoelectric transducers may be directed directly at the pipe wall at an angle or first directly at a reflection wall of said housing so that the longitudinal mode waves transmitted by the piezoelectric transducer to the reflection wall are first converted into shear mode waves which then have a good transfer to the coupling face with the pipe wall so that sonic waves still having sufficient energy are transmitted into the latter. A drawback is, however, that in both cases, energy losses occur as a result of the propagation in the housing and, additionally in the second case, as a result of reflection at the reflection wall.

The object of the invention is to limit the energy losses to a minimum and, at the same time, to provide an ultrasonic flow meter in which, while a good coupling is maintained between transducer housing and pipe wall, the waves transmitted into the latter need to be generated only with very low energy and despite this, can readily be detected. The object of this invention is also to provide an extremely simple and cheap ultrasonic flowmeter.

According to the invention this is achieved in an ultrasonic flow meter of the type mentioned in the introduction in a manner such that the piezoelectric transmitting-receiving transducers each consist of a row of adjacent subtransducers, the pulse emission face of which row is coupled over its entire length in the axial direction to the pipe wall, the subtransducers being activated by control signals, the phase difference between the control signals at every two adjacent subtransducers and the distance between the centres thereof being matched to each other in a manner such that the transducer deforms approximately sinusoidally with a periodic length which corresponds to the wavelength $\lambda$ of Lamb surface waves to be generated in the pipe wall in the $A_o$ mode, which waves propagate in the axial direction along the pipe wall and, on the inside thereof, are converted into longitudinal waves in the adjacent liquid.

In an advantageous embodiment of said ultrasonic flow meter the said phase difference between the signals at the respectively adjacent subtransducers and the distance between the centres thereof are 180° and $\lambda/2$ respectively.

In a further advantageous embodiment of said ultrasonic flow meter each piezoelectric transducer comprises an oblong piezoelement in which the subtransducers are formed by means of crosscuts, made in at least one of the electrodes and situated at said mutual distance from each other.

An ultrasonic flow meter of the inserted type is known from the European Patent Application 0040837. In this type of flow meter the wall of the flow pipe is interrupted in order to fit the two transducers of the flow meter which are situated opposite each other. The sonic waves are transmitted directly to and received directly from the flowing liquid. In this case, the position of the oppositely situated transducer is critical since the beam of sonic waves emitted is narrow. This is largely compensated for because the angle of incidence of the waves into the liquid can be controlled by frequency adjustment. Nevertheless, the position of the receiving transducer remains critical and strict account has to be taken of this in siting the two transducers in this case.

On the other hand, in the flow meter of the clamp-on type according to the invention, the siting is not critical and the transducers to be clamped securely to the outside of the flow pipe can be offset with respect to each other without this affecting the measurement. This is explained in further detail below.

Figure 2:
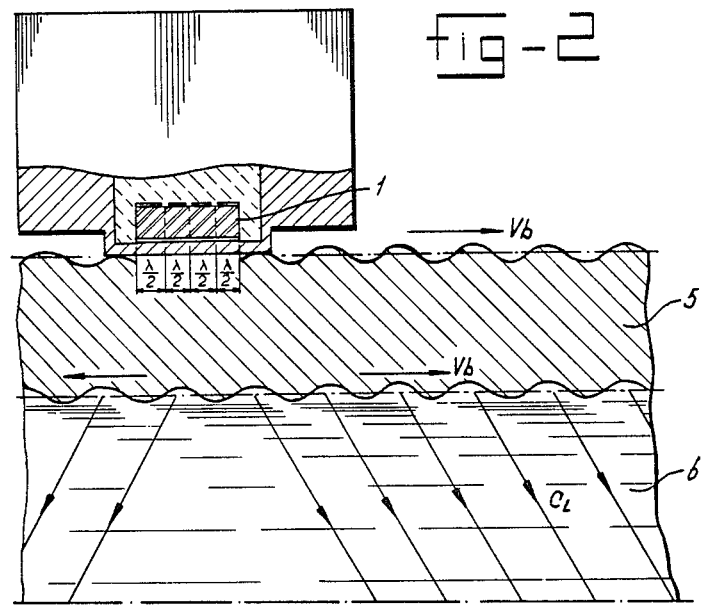
Figure 3:
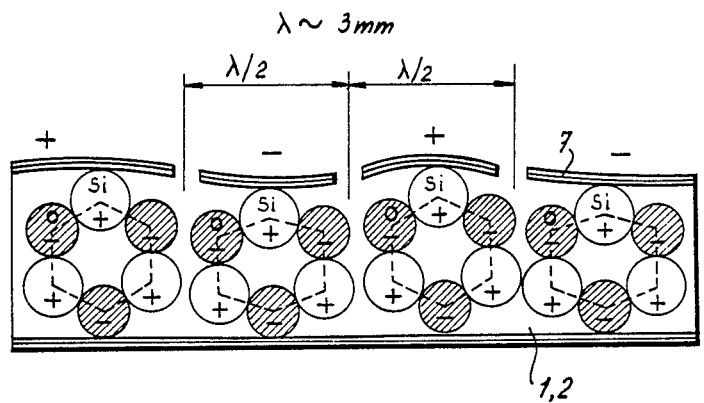
Figure 4:
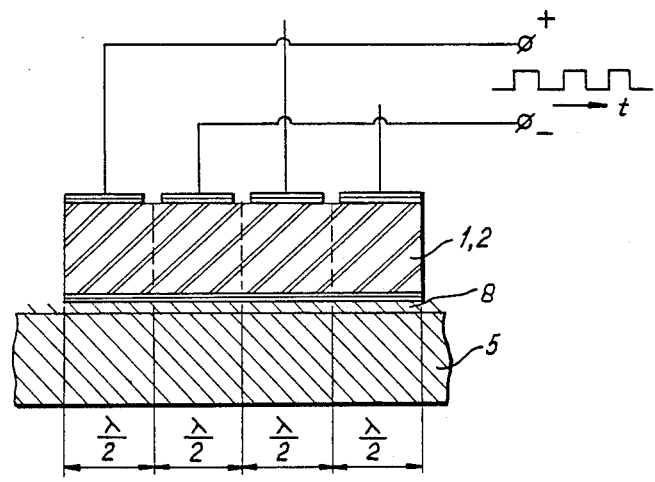

The invention will be explained in more detail on the basis of an exemplary embodiment with reference to the drawings, wherein:

FIG. 1 gives a sectional view of two transmitting-receiving transducers, used in the ultrasonic flow meter according to the invention, which are fitted at both sides of a pipeline axially offset with respect to each other thereon;

FIG. 2 gives a sectional view of a single transmitting-receiving transducer of FIG. 1 sited on the pipe wall;

FIG. 3 gives a diagrammatic sectional view of a part of a transmitting-receiving transducer according to the invention;

FIG. 4 gives a further diagrammatic view of a transmitting-receiving transducer according to the invention; and FIG. 5 gives a block diagram of the electronic control unit used in the ultrasonic flow meter according to the invention.

FIG. 1 indicates how two transducer housings 3 are mounted on a pipeline 5, through which a liquid 6 is flowing, at sites on the pipe wall which are axially offset with respect to each other. Each housing 3 contains a transducer 1 or 2 respectively consisting of a row of subtransducers. Said transducers 1, 2 are fitted on the base face of the housing sited on the pipe wall, while, for example, the rest of the housing is filled with an acoustically damping material 4. On the coupling side of each transducer 1, 2 there is a coupling wall 8 of material which is as thin as possible. This may be, for example, a layer of stainless steel of a few tenths of a millimetre in order to achieve the acoustic coupling with as little transfer loss as possible.

The ultrasonic flow meter according to the invention also includes a standard electronic control unit. This control unit supplies the alternating energization of the transmitting-receiving transducers, the synchronization, the reception and processing of the received pulse signals.

As indicated in FIG. 1, the transducer 1 generates ultrasonic pulses which produce Lamb waves in the $A_o$ mode in a part of the pipe wall. These are shear mode waves which propagate mainly at the surface of the outside and inside of the pipe wall since the amplitude of this type of waves is a maximum at the surface of the pipe wall. These waves can be generated with relatively little energy in the transducer and can also readily be detected by means of the other transducer. The shear mode waves propagating in the surface of the pipe wall on the inside produce in the liquid longitudinal mode waves which propagate in the downstream and upstream direction through the liquid and are received by the transducer 2. The angle of incidence $(\pi/2-\alpha)$ of the waves in the liquid is determined only by the geometry of the pipe wall and the material constants of pipe wall and liquid. The transducer 2 then transmits sonic pulses under the influence of the control unit through the liquid which are received by the transducer 1. The ultrasonic flow meter then determines the difference in the transit times of the sonic pulses in the upstream and downstream direction and determines the flow rate V of the liquid from these in the normal manner.

FIG. 2 indicates diagrammatically how said shear mode Lamb waves at the surface of the outside and inside of the pipe wall propagate at a velocity $V_b$. At the inside of the pipe wall, longitudinal or compression pressure waves are then generated in the liquid by said Lamb waves. Said longitudinal waves form well defined rays which propagate through the liquid at an angle of $(\pi/2-\alpha)$ with respect to the normal to the pipe wall. When said longitudinal waves strike a part of the tube wall, these liquid pressure waves are converted again into Lamb surface waves and then received by the transducer 2.

The transmitting-receiving transducers 1, 2 are, according to the invention, constructed from a number of subtransducers arranged in the form of a row. In contrast to the known embodiments, said subtransducers are in turn sited by means of their emission faces on the base of the transducer housing on the tube wall. The adjacent subtransducers are activated by control signals which differ in phase. The wavelength of the Lamb surface wave to be generated in the tube wall is determined by the phase relationship of the control signals and also the spatial distance between successive subtransducers or elements.

In the simplest form, for example, the subtransducers or elements can be fitted separately in a row next to each other and are activated by control signals which successively have a phase difference of 180°. In this connection the control signals may alternately differ in phase by 180° or the elements may alternately be activated by a fixed voltage and by a signal of particular amplitude. It is also possible to polarize the separate elements alternately in opposite directions and to activate them all with the same signal. The mutual distance of successive centres of the subtransducers in this case corresponds to half the wavelength of the Lamb surface waves in the $A_o$ mode to be generated in the pipe wall.

In a further embodiment, it is possible to construct the transducer not from separate elements but from one whole element, a pattern of electrodes on both sides or on one side of said element being sufficient to cause the whole unit to react as separate transmitting-receiving subtransducers.

FIG. 3 indicates this embodiment according to the invention in which the subtransducers are formed by making cross cuts in one electrode 7 at a mutual distance of $\lambda/2$. Here $\lambda$ is the wavelength of the Lamb surface waves in the $A_o$ mode to be generated in the pipe wall. The cross cuts in the top electrode 7 divide the piezoelectrode into a number of imaginary subelements or subtransducers. A square-wave voltage is applied across the subtransducers as is indicated in FIG. 4. The piezoelement then deforms approximately sinusoidally as indicated in FIG. 3 with a periodic length corresponding to the wavelength $\lambda$ of the Lamb waves in the $A_o$ mode.

It is also possible to provide the subtransducers or the the said cross cuts at a distance from each other other than the said $\lambda/2$. By matching the phase difference between the control signals to this and by adjusting it to a value other than 180°, the required Lamb surface waves in the $A_o$ mode can again be generated.

A very cheap and simple flow meter is ultimately obtained by means of all these above-mentioned embodiments of the transducer.

As a result of this siting of the transducers with their emission faces directly on the base of the transducer housing and then directly on the pipeline and by matching the distance between the subtransducers, it is possible to generate and receive in a selective manner Lamb surface waves in the $A_o$ mode in the tube wall. With respect to the known transducers used in industry, these ultrasonic waves are generated with very low energy in the transmitting transducer and they are also received in an unambiguous manner by the receiving transducer. The amount of noise and parasitic waves is extremely low. As a result, the energy ratio between the transmitted electric pulse and the received electric pulse is large, the electrical energy at the same time being converted in an efficient manner into mechanical power and vice versa.

Because surface waves are produced at the receiving side over a relatively large region on the outside surface of the pipe wall, the definition of the position of the receiving transducer is not critical. After installing and securely clamping the transducers, the fixed transit times of the sonic signal in the transducer and in the solid walls are allowed for electronically in the control unit by the adjustment of dead times.

The ultrasonic flow meter according to the invention can be used on pipelines of different material. Matching to said material takes place by altering the mutual distance between the cross cuts in the electrode of the transducer.

Reference is now made to FIG. 5 in which a block diagram of the said electronic control unit is indicated. The pulse generator 12 is controlled from the central clock circuit or microprocessor 10 so as to alternately energize the upstream transducer 1 and the downstream transducer 2. At the same time, the transmitting-receiving switch 13 is energized from the microprocessor. After switching over the transmitting-receiving switch 13, the pulses received are fed to the amplifier 14 and then to the time measuring circuit 15. In the microprocessor 10 which is equipped with a memory 11, the determination of the flow rate is then carried out on the basis of the data fed in by the input unit 16, such as dead time, pipe material, pipe diameter, etc. An indication of the flow rate is then delivered via the output circuit 17 to the output 18.

We claim:

1. An ultrasonic flow meter for the measurement of the flow rate of a liquid in a pipeline comprising:
two piezoelectric transmitting-receiving transducers, each having a housing with means for attachment to a pipeline, said attachment being on opposite sides thereof, and in axially offset positions with respect to each other, said transducers alternatively transmitting ultrasonic pulses into the pipeline and receiving ultrasonic pulses therefrom in order to determine the flow rate from the transit time of the sonic pulses in the upstream and downstream directions;

each piezoelectric transmitting-receiving transducer comprising a row of adjacent subtransducers, the pulse emission face of which row is coupled over its entire length in the axial direction to the pipe wall;

means to produce control signals to activate the subtransducers, the phase difference between the control signals at every two adjacent subtransducers and the distance between the centers thereof being matched to each other in a manner such that the transducer deforms approximately sinusoidally with a periodic length which corresponds to the wavelength of Lamb surface waves to be generated in the pipe wall in the $A_o$ mode, which waves propagate in the axial direction along the pipe wall and, on the inside thereof, are converted into longitudinal waves in the adjacent liquid.

2. Ultrasonic flow meter according to claim 1, in which the phase difference between the signals at the respectively adjacent subtransducers and the distance between the centers thereof are 180° and $\lambda/2$ respectively.

3. Ultrasonic flow meter according to claim 1, in which each piezoelectric transmitting-receiving transducer comprises an oblong piezoelement in which the subtransducers are formed by means of crosscuts, made in at least one of the electrodes and situated at said mutual distance from each other.

4. The meter of claim 1 in which the means for attachment is a clamp-on means.

* * * * *